United States Patent [19]

Zolton et al.

[11] Patent Number: 4,597,966
[45] Date of Patent: Jul. 1, 1986

[54] HISTIDINE STABILIZED IMMUNOGLOBULIN AND METHOD OF PREPARATION

[75] Inventors: Raymond P. Zolton, Somerville; Jennifer A. Nasser, Piscataway, both of N.J.

[73] Assignee: Ortho Diagnostic Systems, Inc., Raritan, N.J.

[21] Appl. No.: 689,882

[22] Filed: Jan. 9, 1985

[51] Int. Cl.$^4$ .......................................... A61K 39/395
[52] U.S. Cl. ...................... 424/85; 424/101; 530/387
[58] Field of Search ............... 260/112 B; 424/85, 101

[56] References Cited

U.S. PATENT DOCUMENTS

| | | | |
|---|---|---|---|
| 4,093,606 | 6/1978 | Coval | 260/112 B |
| 4,124,576 | 11/1978 | Coval | 260/112 B |
| 4,360,457 | 11/1982 | Ono et al. | 260/112 B |
| 4,362,661 | 12/1982 | Ono et al. | 260/112 B |
| 4,384,993 | 5/1983 | Sato et al. | 260/112 B |
| 4,434,093 | 2/1984 | Zolton et al. | 260/112 B |
| 4,439,421 | 3/1984 | Hooper et al. | 424/85 |
| 4,440,679 | 4/1984 | Fernandes et al. | 424/85 X |
| 4,477,432 | 10/1984 | Hardie | 424/85 |

OTHER PUBLICATIONS

Gerber, J. Immunol. 92, 885–888(1964).
Gerber, Arthritis Rheum. 17, 85–91(1974).

Primary Examiner—Howard E. Schain
Attorney, Agent, or Firm—Mark A. Hofer

[57] ABSTRACT

Histidine-stabilized immunoglobulin preparations and a method for their manufacture are disclosed. The present invention is particularly well suited for stabilization of human gamma globulin (IgG) preparations having a relatively low protein content. Preferred stabilized human gamma globulin preparations comprise about 5 wt-% or less gamma globulin, histidine at a concentration of about 0.025M to about 0.2M, and optionally glycine at a concentration of about 0.05M to about 0.5M. The pH value of the preparations is at least 6.0 but not more than 7.0. A pH value of about 6.4 is most preferred. Conductivity of the preparations is about 2 to about 4 millisiemens at 5° C., preferably about 2.5 to about 3.5 millisiemens at 5° C., and most preferably about 2.7 millisiemens at 5° C.

19 Claims, No Drawings

HISTIDINE STABILIZED IMMUNOGLOBULIN AND METHOD OF PREPARATION

TECHNICAL FIELD

This invention relates to stabilized immunoglobulin preparations. One aspect of this invention relates to stabilized highly purified immunoglobulin G preparations intended for injection into humans.

BACKGROUND OF THE INVENTION

Under appropriate circumstances the injection of an antigen into an animal produces a specific antiserum that reacts selectively with the antigen. This antiserum contains proteins that are responsible for the recognition of the antigen, i.e., proteins that possess a so-called "antibody function." Such proteins are commonly referred to as "antibodies" or, in a broader sense, as "immunoglobulins" (Ig).

All individuals within a given species have in common various Ig categories called "isotypes." For example, in humans 10 isotypes have been identified and grouped into five classes, namely IgG, IgM, IgA, IgD and IgE, which classes are further subdivided into subclasses, e.g., $IgG_1$, $IgG_2$, $IgG_3$ and $IgG_4$ for Immunoglobulin G. These classes are also sometimes referred to or designated as $\gamma G$, $\gamma M$, $\gamma A$, $\gamma D$ and $\gamma E$, respectively. The predominant serum immunoglobulins are of the class IgG or gamma globulins.

Gamma globulin (IgG) preparations intended for injection into humans originally were produced by the alcohol fractionation procedure developed by Dr. E. Cohn and coworkers of Harvard during the 1940's: This procedure is described in Cohn et al., J. Amer. Chem. Soc. 68:459 (1946). These preparations were prepared as 10-18 wt-% protein solutions, the most common being a 15 wt-% protein solution. The latter was favored since at that concentration, the product exhibited the same viscosity as blood. Another advantage for these high protein gamma globulin products was their inherent shelf stability as judged by the absence of visually observable precipitation upon storage at 2°-8° C. for time periods of 2-3 years. In contrast, preparations containing less than about 10 wt-% protein frequently exhibited visually observable precipitation in the final liquid product.

The foregoing, relatively high protein gamma globulin products initially were intended for intravenous (IV) administration. The latter is considered advantageous clinically because immediate high levels of circulatory protective antibodies are attainable, whereas approximately one-half of the antibody given intramuscularly (IM) is lost due to local proteolysis and incomplete absorption. Unfortunately, experience has shown the above product not to be safe for IV administration due to adverse anaphylatic reactions in recipients. See, for example, Bowman, Clin. Obst. Gynec. 25:341 (1982) and Schroeder et al., Amer. J. Med., Mar. 30, 1984, page 33. The formation of aggregated gamma globulin polymers during storage of products prepared by the standard cold alcohol procedure allows for these aggregates to combine with complement in the patient's blood and to produce an anticomplement reaction. Thus, all gamma globulin products produced by the standard cold alcohol procedure have been approved only for intramuscular use.

The formation of relatively large molecular weight aggregates of gamma globulin in aqueous solutions is particularly deleterious to its pharmaceutical utility. Such denaturation is believed to be influenced by sulfhydryl-disulfide interchange reaction.

The ability of gammaglobulin to bind complement is greatly increased as a result of denaturation, in particular by aggregation to high molecular weight species. The complement binding mechanism of these aggregates appears to be identical to that of antigen-antibody complexes. Marcus, D. M., (1960) J. Immunol. 84:273-284. In the case of IgG, it is known that the complement binding site requires two molecules close together. It is therefore possible that critical packing of the molecules is required, rather than any necessary conformational change. However, the size distribution of aggregates in denatured antibody solutions and its relation to anticomplement activity has not been examined.

In earlier studies, Gerber, J. Immunol. 92:885-888(1964) and Gerber, Arthritis Rheum. 17:85-91(1971), it is postulated that in patients suffering from rheumatoid arthritis there is an in vivo mechanism triggered by metallic copper that causes increased formation of aggregate of gamma globulin. This worker found a beneficial effect to the patient if the level of one amino acid, L-histidine, was increased. These studies were done at physiological pH values, i.e, a pH of about 7.4 however. Also, the effect of histidine protection on relatively low protein human gamma globulin products in the area of absence of aggregate and anticomplementary activity was not examined in the studies by Gerber and cannot be predicted from the reported data.

As gamma globulin therapy has become an accepted practice, the demand for large quantities of commercial product worldwide has required manufacturers to adopt hyperimmunization programs for donors of the starting blood from which the gamma globulin-containing product is derived. The resulting plasma or serum has a desired higher starting antibody titer. Hence, more product can be derived from a fixed starting volume of blood. While the desired final antibody titer can also be attained at a lower protein concentration than the previous 10-18 wt-% value, such gamma globulin-containing products are less stable during storage.

Thus, one must either add protein to the product to maintain the desired 10-18 wt-% concentration, or develop methods for stabilizing a solution of the highly purified gamma globulin product having a protein concentration of less than 10 wt-%. For the former approach, it is common to add either purified albumin or gamma globulin derived from a low titer plasma source. However, this approach is not economically attractive. Also, it exposes the patient to additional health risks since viral contaminants from the additional purified proteins are a possibility. An example of the latter approach can be found in U.S. Pat. No. 4,186,196 to Lundblad et al. where a relatively high concentration of maltose is added to the final buffer to stabilize a 5 wt-% gamma globulin product. The latter is derived from a modified cold alcohol procedure that is said to remove aggregates as well, the objective being a product that can be administered intravenously.

Other prior attempts at stabilization of protein solutions are illustrated by U.S. Pat. No. 2,826,533 to Fowell which discloses the use of dextrose to increase the solubility of fibrinogen in solution, U.S. Pat. No. 4,089,949 to Thomas which discloses the use of a variety of carbohydrates (e.g., dextrose, mannose, galactose, fructose, lactose, sucrose and maltose) to enhance the solubility of an anti-hemophilic factor (AHF)-fibrinogin composition, and U.S. Pat. No. 3,057,781 to Mace et al. which discloses stabilization of plasma with invert sugar.

Other workers have explored the possibility of producing a gamma globulin product by an entirely different process, again with an objective to produce a product suitable for IM or IV administration. The approach currently favored employs ion-exchange chromatography. See, for example, U.S. Pat. No. 4,136,094 by Condie and Hoppe et al., Vox Sang. 25:308 (1973); Friesen et al., J. Applied Biochem. 3:164 (1981); and Walsh and O'Riordan, Irish Med. J. 75:232 (1982).

Condie contends that an IV administratable and stable 5 wt-% protein solution is possible without extra additives beyond the standard glycine-saline buffer. It should be noted, however, that a key step in this particular process is the pretreatment of the plasma source with colloidal silica. The present process, on the other hand, does not require exposure by workers to the potential health hazard of working with silica fumes while preparing a stabilized protein solution. The other three references of the foregoing grouping rely exclusively on the ion-exchange chromatography process to produce a final product said to be safe for IV administration. However, all three require that the final product, which contains very low protein concentration (1-4 wt-%), be lyophilized to meet adequate shelf stability requirements. The present invention, on the other hand, provides a relatively low cost procedure for amply stabilizing low protein gamma globulin solutions that avoids the inconvenience and expense of lyophilization and reconstitution prior to use.

To evaluate the stability of liquid gamma globulin products, a relatively simple test has been used historically. This test is recommended by the U.S. Bureau of Biologics and involves heating the finished product to a temperature of 57° C. and holding it at that temperature for four hours while examining the product for visual precipitates. See Code of Federal Regulations 21, Food and Drugs, 640.101a (revised April 1978). Fernandes and Lundblad, Vox Sang. 39:101–112 (1980) report a modification of this procedure suitable for routine evaluation of potential additives. The modified procedure comprises heating approximately 2 milliliters of the test product at 57° C. for four hours and then evaluating the percent change in degree of opalescence as measured by recording the transmittance at 580 nm with a laboratory spectrophotometer.

The preferred buffer for purified liquid gamma globulin products heretobefore has been glycine-saline, pH 6.4–7.2; however, this buffer has now been found to be inadequate if the protein concentration is 5 wt-% or less.

Another problem encountered with relatively low protein gamma globulin products which employ only glycine-saline as the stabilizer is pH control. Historically, the higher protein concentration (i.e. about 15 wt-%) has served as the principal buffering agent for the product, not either glycine or saline. Yet the relatively lower protein concentrations do not exhibit an adequate buffering effect.

The present invention, on the other hand, provides superior pH stabilization over the historical glycine-saline buffer for purified gamma globulin solution with a protein concentration of 5 wt-% or less.

Additionally, this invention provides a relatively low cost product which is safe when injected into patients for purposes of gamma globulin therapy. The present product is effective at much lower concentrations than the previously used, stabilized products, does not require the use of hazardous chemicals like silicon dioxide to treat the gamma globulin, and does not require chemical modifications of the gamma globulin itself.

SUMMARY OF THE INVENTION

Immunoglobin preparations containing a stabilizing amount of histidine and having a pH value in the slightly acidic range are contemplated by the present invention. Such preparations are substantially free from anticomplement activity and contain histidine at a concentration sufficient to inhibit aggregation of the immunoglobulin that is present.

The pH value of the present preparations is at least about 6.0 but not more than 7.0, preferably about 6.2 to about 6.6, and most preferably about 6.4.

Conductivity of the present preparations is in the range of about 2 to about 4 millisiemens (mS) at 5° C., preferably about 2.5 to about 3.5 millisiemens at 5° C., and most preferably about 2.7 millisiemens at 5° C.

While any immunoglobulin can be stabilized for storage in the foregoing manner, the present invention is particularly well suited for the stabilization of human gamma globulin or IgG, the predominant serum immunoglobulin in human plasma.

To that end, a particularly preferred stabilized, sterile gamma globulin composition, exhibiting substantially no anticomplement activity, comprises an aqueous solution containing a pharmacologically effective concentration of gamma globulin, histidine in a concentration sufficient to inhibit gamma globulin aggregation, and glycine in a concentration of about 0.05M to about 0.5M.

In the foregoing composition the gamma globulin concentration is about 5 weight percent or less, more preferably about 0.05 to about 5 weight percent, and most preferably about 1 to about 2 weight percent.

Stabilized immunoglobulins can be administered to a patient intravenously or intramuscularly and are useful for elevating the circulating antibody levels of a patient.

DETAILED DESCRIPTION OF PREFERRED EMBODIMENT

Buffering ability and pH are important aspects of the present invention because the solubility of most globular proteins, such as the immunoglobulins, is influenced by the pH of the system in which the protein is present. Usually the pH at which a protein is least soluble is its isoelectric point, i.e., that pH value at which the protein molecule has no set electric field. At the isoelectric pH there is no electrostatic repulsion between neighboring protein molecules, and they tend to coalesce and precipitate. In practicing the present invention it is believed that the immunoglobulins present, e.g., the gamma globulins, are stabilized against aggregation by maintaining the solution pH at a value other than the isoelectric pH value of the immunoglobulin molecules present.

To that end the amino acid histidine is utilized as a stabilizing agent. Preferably, histidine is used together with glycine. The histidine and glycine used to stabilize the present aqueous solutions are described in detail in, for example, The Merk Index, Tenth Edition, Merk & Co., Inc. Rahway, N.J. (1983) at pages 4621 and 4359, respectively. L-Histidine is the particularly preferred stereoisomer of histidine for present purposes, but D-histidine or a racemic mixture of histidine stereoisomers are also suitable. In addition, the pharmaceutically acceptable salts of histidine and glycine can be used as well. L-histidine hydrochloride monohydrate and glycine hydrochloride are particularly preferred salts for present purposes.

The phrase "pharmaceutically acceptable salts", as used herein, refers to non-toxic alkali metal, alkaline earth metal and ammonium salts used in the pharmaceutical industry, including the sodium, potassium, lithium, calcium, magnesium and ammonium salts and the like that are prepared by methods well-known in the art. This phrase also includes non-toxic acid addition salts that are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and the like.

The concentrations of histidine and glycine in the present preparations can vary depending on such factors as salt concentration, etc. The concentration of histidine preferably is in the range of about 0.025M to about 0.2M and the concentration of glycine, if present, can be in the range of about 0.05M to about 0.5M. In a particularly preferred composition the concentrations of histidine and glycine are about 0.05M and about 0.1M, respectively.

One of the advantages of the present invention is its ability to buffer the aqueous solution adequately against undesirable changes in hydrogen ion concentration (pH). The overall range of pH values for the present preparations is at least about 6.0 to no greater than 7.0. In preferred embodiments, the pH value of the aqueous preparations embodying the present invention is about 6.2 to about 6.6, more preferably about 6.4.

The buffering capacity in the present preparations is believed to be provided for the most part by histidine, the only amino acid with significant buffering capacity in the desired pH range.

Conductivity of the aqueous immunoglobulin solutions is also important for optimum stability. To this end, the present solutions exhibit a conductivity of about 2 to about 4 millisiemens at 5° C., plus or minus 10%. Preferably, the solution conductivity is about 2.5 to about 3.5 millisiemens at 5° C., most preferably the conductivity is about 2.7 millisiemens at 5° C.

When L-histidine hydrochloride monohydrate is used as the stabilizing agent and the final pH adjustment is made using an aqueous sodium hydroxide solution, a pH adjustment to about 6.4 will result in a sodium chloride concentration in the final solution of about 0.05M and the desired conductivity of 2.7±0.27 millisiemens at 5° C.

The immunoglobulin, e.g., gamma globulin, is present in the preparations embodying this invention in a pharmacologically effective concentration. The specific amount can vary, depending upon the intended route of administration and therapeutic use; however, in general the immunoglobin concentration in the present preparations is about 0.05 to about 5 weight percent, preferably about 1 to about 2 weight percent.

In the case of gamma globulin, the native protein preferably is at least about 95 percent pure, more preferably about 99.5 percent pure, and has not undergone any chemical or enzymatic modification.

Gamma globulin stabilized in accordance with the present invention can be administered intravenously to patients for therapeutic purposes in single or multiple unit doses ranging from about 20 milligrams/kg/day to about 200 milligrams/kg/day over a desired time period. For intramuscular administration the individual doses are somewhat larger. The present preparations can be administered to a patient in conjunction with surgical or chemical treatments as well.

The term "unit dose" refers to physically discrete units suitable as unitary dosages for warm blooded animals, each unit containing a predetermined quantity of active material calculated to produce the desired therapeutic effect in association with the preparation of this invention. The specifications for the novel unit dose of this invention are dictated by and are directly dependent on (a) the unique characteristics of the active material, (b) the particular pharmacological or therapeutic effect to be achieved, and (c) the limitations in the art of compounding such active material for use in animals as disclosed in detail in the present specification, these being features of the present invention.

The immunoglobulins suitable for compounding the present compositions can be derived from any source as long as the desired purity standards are met. Various immunglobulin recovery and purification techniques are known in the art, such as ion exchange resin techniques, affinity chromatography, and the like, and are well suited for the purposes of this invention. See, for example, U.S. Pat. No. 4,434,093 to Zolton et al., co-pending patent application U.S. Ser. No. 680,191, filed on Dec. 10, 1984 by Zolton et al., and Stanworth, Nature 188:156-157(1960).

In general, the preparations of this invention are compounded by providing an aqueous solution of the desired immunoglobulin, e.g., human gamma globulin, at the requisite concentration and purity, and then combining therewith histidine in an amount sufficient to inhibit aggregation of the immunoglobulin that is present. The hydrogen ion concentration of the resulting solution is adjusted to a pH value of at least about 6.0 but not more than 7.0. Optionally, glycine can also be added in the amounts stated hereinabove. Likewise, if needed, conductivity of the resulting solution is adjusted to the hereinabove-stated limits in a manner known in the art.

The present invention is further illustrated by the following detailed examples.

EXAMPLE 1

Preparation of Human Plasma Pool

Blood units were collected from a large number of Rh-negative donors who had been previously hyperimmunized with Rh-positive red cells. Each unit was centrifuged by standard procedures to produce platelet-poor plasma. The latter was frozen individually within 4 hours of the collection. These units were stored frozen until needed. The frozen units were thawed and pooled together on the day the fractionation was to start. Cryoprecipitate observed to be present in the thawed plasma was removed from the plasma after pooling and by standard procedures. The obtained supernate from this process contained the desired gamma globulin and was held at 2°–8° C. to await further fractionation.

EXAMPLE 2

Sample Preparation Prior to Ion-Exchange Chromatography

The supernate (5.8 l) prepared in Example 1, above, contained a starting anti-D activity of 73.7 ug/ml and was dialyzed using a Millipore ultrafiltration unit and the column equilibration and running buffer, i.e., 0.05M imidazole-0.023M sodium chloride buffer, pH 7.5±0.1. Two volumes were exchanged. This step insured that when the plasma sample was subsequently applied to a column containing an ion-exchange resin the conductivity state of the plasma was such that the resin neither expanded nor contracted. The dialyzed sample was held at 15°-20° C. prior to start of the next step. The volume of the dialyzed sample was 5.4 liters.

EXAMPLE 3

Ion Exchange Chromatography

QAE-Sephadex, A-50 anionic resin (800 g dry weight; Lot 12773), was washed, swollen and equilibrated with the buffer characterized in Example 2, above, per instruction of its manufacturer, Pharmacia Fine Chemicals, Piscataway, N.J. An equilibrated resin slurry was obtained and was loaded into a plastic column (15.0 cm high×37.0 cm diameter) to provide a final bed volume of 16.0 liters. The dialyzed plasma sample from Example 2, above, was applied to this packed column and allowed to flow down through the resin bed therein at a flow rate of 1.5 liters/hour and at a temperature of 20±5° C. During this procedure the majority of the plasma proteins bind to the positively charged ion while most of the gamma globulin product does not bind and hence passes directly out the bottom of the column where it is recovered.

After all of the plasma sample had entered the resin bed, the aforesaid column buffer was continuously passed through the column. The effluent from the column was monitored for the presence of protein by measuring $OD_{280nm}$ (optical density at 280 nanometer wavelength) readings on a standard laboratory spectrophotometer. The latter readings were referenced to that of the column buffer by itself. Collections of effluent aliquots were initiated when a rising 280nm reading was observed. The collection was continued until the $OD_{280nm}$ readings returned to 20-30% of the initial baseline reading. The collected product, rich in gamma globulin, was observed to have a volume of 17.85 liters and a protein concentration of less than 0.1% by weight. The recovery of the anti-D activity was observed to be approximately 80%. The obtained dilute gamma globulin product was held at 2°-8° C. until it could be concentrated to a desired antibody potency of 250 +25 ug Anti-D/ml.

EXAMPLE 4

Concentration of Product

The dilute product obtained in Example 3, above, was concentrated approximately 20 times using a Millipore ultrafiltration unit equipped with a 10,000-molecular weight cut-off membrane.

EXAMPLE 5

Dialysis of Final Product With Stabilizer Solution

After concentration as described in Example 4, above, and while still in the same ultrafiltration unit, the concentrated product volume was exchanged four times with the present stabilizer solution, i.e., 0.05M histidine-0.1M glycine, pH 6.4±0.1. The final volume or the concentrated product was measured to be 1.35 liters. The protein concentration in the concentrated product was observed to be 1.4% by weight, and having a pH of 6.4±0.1 and conductivity of 2.7 millisiemens ±0.27 at 5° C.

EXAMPLE 6

Sterile Filtration and Vialing

The concentrated product stabilized in Example 5, above, and having antibody potency as reported in Example 3, above, was sterile-filtered through a 0.22 micron filter and vialed at a final volume of 1.2 ml/vial. The filled vials were stoppered, sealed, and stored at 2°-8° C. for three years. Some aliquots of the concentrated and stabilized product were lyophilized prior to storage and then stored in lyophilized state. Upon repeat testing over three years the histidine-stabilized and stored product has been observed to be free of aggregates and anti complementary activity, and therefore is safe for IV injections.

Histidine and glycine are readily available in pure form and have good stability in aqueous solutions. Physiologically, they are safe and are used as dietary supplements in powdered protein preparations. However, the present invention contemplates a novel combination of histidine and glycine and, given the unpredictability of biological systems, their use as stabilizing solutes for the purposes of the present invention was examined in safety studies as reported hereinbelow.

EXAMPLE 7

Safety Study of Histidine and Glycine Solutions in Mice

A histidine and glycine solution (0.05M L-histidine hydrochloride monohydrate, 0.010M glycine, 0.003% thimerosal, in pyrogen free water; pH 6.4±0.1; conductivity 3.0±0.3 mS at 0° to 5° C.) was tested intramuscularly in comparison with a glycine and saline solution (0.20M glycine, 0.05M sodium chloride, 0.01% thimerosal, in pyrogen free water; pH 7.45±0.15; conductivity 3.0±0.1 mS at 0° to 5° C.) and a saline control solution (0.90% sodium chloride, 0.003% thimerosal, in pyrogen free water; pH 6.4±0.1).

Each solution was administered by injecting 0.2 ml into the thigh muscle of mice 3 times per week for two weeks. This dosage level was calculated to exaggerate the human single dose exposure by at least 1000 times. All mice survived the 2-week test and had no untoward chemical effects associated with the treatment. One mouse receiving the glycine-saline solution lost weight (one gram) during the test period. This was deemed to be an insignificant weight loss.

At necropsy little reaction was observed in the intramuscular injection sites and no visceral tissue change associated with treatment was present. Microscopic examination of the selected tissues (e.g., lungs, heart, liver, spleen, kidneys and injection sites from both rear legs) revealed no effect associated with the various injected solutions. The only injection site changes were associated with needle puncture trauma.

EXAMPLE 8

Safety Study of Histidine and Glycine Solutions in Guinea Pig

The same solutions as were used in the study reported in Example 7, above, were utilized in a 14-day intradermal safety study with guinea pigs. A 5 wt-% L-histidine hydrochloride monohydrate solution in pyrogen-free water, adjusted to a pH value of 6.4±0.1, was utilized as well. Each test solution was injected into five adult female guinea pigs (Hartly Descendant; 400+ grams in weight) that had been quarantined for at least 7 days.

The back of each animal was shaven five days prior to the first injection. Each animal was dosed three times (on Day 1, Day 10 and Day 14) with 0.1 cc of test solution, on the back, near the midline.

The animals were observed daily for any abnormality. The injection sites for each animal were observed at 24 and 48 hours post injection for redness or swelling.

During the course of this study no reaction to the test solutions was noted. While one guinea pig receiving the histidine-glycine test solution became ill with a cold during the test period (diarrhea, weight loss, chills, nasal discharge), this animal had no observable reaction to the injected test solution.

Various comparative studies have been carried out with the stabilized preparations embodying the present invention. These studies and the results thereof are set forth in Tables I through V that follow.

TABLE I

HIGH PERFORMANCE LIQUID CHROMATOGRAPHY (HPLC) PROFILE OF STABILIZED LIQUID LOW PROTEIN GAMMA GLOBULIN PRODUCT

| | HPLC Results[c] | | |
|---|---|---|---|
| | % Monomer | % Dimer | % Aggregate |
| Control[a] | 84.242 | 15.009 | 0.112 |
| Purified human gamma globulin[b] stabilized by 0.05 M L-histidine-0.1 M glycine, pH 6.4, stored as liquid product at 2–8° C. | 100.000 | 0.000 | 0.000 |
| Purified human gamma globulin[b] stabilized by 0.05 L-histidine-0.1 M glycine, pH 6.4, stored as a lyophilized product at 2–8° C. | 100.000 | 0.000 | 0.000 |

[a]The control was a commercially available, 15.0% by weight protein human gamma globulin product derived from cold alcohol process. This sample was expected to contain measurable levels of all three components.
[b]Method used to produce purified gamma globulin was ion-exchange chromatography as described in Examples 1–6, above. The same source was used for both samples. The final protein concentration was 1.4% by weight. Both samples were stored unopened 24 months at 2–8° C.
[c]High performance liquid chromatography (HPLC) assay was done using a TSK-3000 SW column based on the published report by Bertolini, Vox Sang. 43:87 (1982). The flow rate was 0.5 ml/min and the detector wavelength was set at 280 nm. The aggregates, where present, were observed to elute at approximately 13.6 minutes followed by a dimer peak at approximately 16.5 minutes and a monomer peak at approximately 19.5 minutes.

Data in Table I show that during a two-year storage period L-histidine stabilized gamma globulin does not exhibit appreciable aggregate formation.

TABLE II

RESULTS FROM HEAT-STRESS TESTING[a]

| Sample | % Transmission Change |
|---|---|
| I. Comparison of Various Buffers on the Stability of Purified Human Gamma Globulin (IgG) Derived from the Standard Cold Alcohol Process | |
| "A" 3 wt % IgG in 0.2 M glycine-0.05 M sodium chloride, pH 6.4. | >90.0 |
| "B" 3 wt % IgG in 0.025 M histidine-0.2 M glycine, pH 6.4. | 6.7 |
| "C" 3 wt % IgG in 0.05 M histidine-0.2 M glycine, pH 6.4. | 6.7 |
| II. Comparison of Various Buffers on the Stability of Purified IgG Derived from an Ion-Exchange Chromatography System | |
| "D" 2.0 wt % IgG in 0.2 M glycine-0.05 M sodium chloride, pH 6.4. | 24.0 |
| "E" 2.0 wt % IgG in 0.1 M histidine, pH 6.4. | 7.6 |
| "F" 2.0 wt % IgG in 0.05 M histidine-0.1 M glycine, pH 6.4. | 5.4 |
| III. Relative Effect of Various Agents on Heat-Stress Stability of Purified IgG Derived from an Ion-Exchange Chromatography System | |
| "G" 2.5 wt % IgG stabilized by 0.2 M glycine-0.05 M sodium chloride, pH 6.4. | 23.6 |
| "H" 2.5 wt % IgG stabilized by 0.2 M glycine-0.05 M sodium chloride and 0.5 wt % tryptophan, pH 6.4. | 23.6 |
| "I" 2.5 wt % IgG stabilized by 0.2 M glycine-0.05 M sodium chloride and 0.5 wt % phenylalanine, pH 6.4. | 20.8 |
| "J" 2.5 wt % IgG stabilized by 0.2 M glycine-0.05 M sodium chloride and 0.001 wt % cysteine, pH 6.4. | 19.7 |
| "K" 2.5 wt % IgG stabilized by 0.2 M glycine-0.05 M sodium chloride and 10 wt % maltose, pH 6.4. | 5.0 |
| "L" 2.5 wt % IgG stabilized by 0.2 M glycine-0.05 M sodium chloride and 10 wt % sucrose; pH 6.4. | 6.5 |
| "M" 2.5 wt % IgG stabilized by 0.1 M glycine-0.05 M histidine, pH 6.4. | 5.4 |

| Sample | Final pH | % Transmission Change |
|---|---|---|
| IV. Evaluation of the Effect of pH on Stabilizer Performance | | |
| "N" 2.5 wt % IgG in 0.05 M histidine-0.1 M glycine | 6.4 | 5.4 |
| "O" 2.5 wt % IgG in 0.05 M histidine-0.1 M glycine[b] | 7.2 | 69.0 |
| "P" 2.5 wt % IgG in 0.02 M sodium phosphate | 6.4 | off-scale; noted 17.0% change after |
| | 6.4 | 2 hours. |

[a]Heat stress testing was done according to the procedure outlined by Fernandes and Lundblad in Vox Sang. 39, 101 (1980).
(b)pH Adjustment was made by the addition of aqueous NaOH solution, q.s.

The data set forth in the above Table demonstrate that a glycine-saline buffer is not adequate for the stabilization of purified liquid gamma globulin products were the protein concentration is relatively low. The foregoing data also underscore the unexpected advantages from utilizing histidine to stabilize such products at a pH value in the slightly acidic range.

TABLE III

MEASUREMENT OF ANTICOMPLEMENTARY ACTIVITY IN AGED STABILIZED LOW PROTEIN PRODUCT

| | Anticomplementary Titer[a] |
|---|---|
| Control Sample | 1:64 |
| Stabilized Product[b] (stored 6 months at 2–8° C.) | less than 1:2 |
| Stabilized Product[b] | less than 1:2 |

TABLE III-continued
MEASUREMENT OF ANTICOMPLEMENTARY ACTIVITY IN AGED STABILIZED LOW PROTEIN PRODUCT Anticomplementary Titer[a]

(stored 2 years at 2-8° C.)

[a]The anticomplementary activity of the above-identified globulin was determined by the method described by Friesen et al., J. Applied Biochemistry, 3:164–175 (1981). Serial twofold dilutions of the IgG solution were incubated with 5 $CH_{50}$ units of complement. Following overnight incubation at 4° C., 1% sensitized sheep blood cells were added and incubated at 37° C. for 30 min. The anticomplementary activity was expressed as the protein concentration milligrams per milliliter of the dilution showing at least 50% hemolysis.

[b]This product was prepared with ion-exchange purified human gamma globulin as described in Examples 1–6. Final protein concentration of sample was 1.4% by weight. The product was stored in a sealed container as a liquid.

The data in Table III show that the compositions stabilized in accordance with the present invention exhibit substantially no anticomplementary activity.

TABLE IV
EFFECT OF IgG CONCENTRATION ON BUFFERING CAPACITY OF STANDARD GLYCINE-SALINE BUFFER

| % IgG (by Weight)[a] | pH[b] |
|---|---|
| 0 | 6.40 |
| 0.40 | 6.75 |
| 1.00 | 6.90 |
| 1.80 | 6.95 |
| 2.50 | 6.95 |
| 2.75 | 7.00 |
| 3.80 | 7.00 |

[a]Samples used ion-exchange purified human gamma globulin as described in Examples 1–5. Dried product was added in various amounts to the standard glycine-saline buffer, 0.2 M–0.05 M, pH 6.4.
[b]pH Was measured at 20–25° C. by standard laboratory procedures.

The data in Table IV demonstrate that the buffering capacity of the standard glycine-saline buffer is inadequate for the tested protein concentrations. Had the buffer capacities been adequate, no change in the PH value of the samples would have been observed.

TABLE V
EFFECT OF DIFFERENT LEVELS OF GLYCINE IN FINAL STABILIZING BUFFER

| Sample[a] | HPLC Results[b] | | |
|---|---|---|---|
| | % Monomer | % Dimer | % Aggregate |
| Purified human gamma globulin stabilized by 0.05 M histidine-0.01 M glycine, pH 6.4 | 99.820 | 0.170 | 0.004 |
| Purified human gamma globulin stabilized by 0.05 M histidine-0.47 M glycine, pH 6.4. | 99.882 | 0.111 | 0.002 |

[a]Method used to produce purified gamma globulin was ion-exchange chromatography as shown in Examples 1–6, above. The same source was used for both samples. The final protein concentration was 1.2% by weight. Both samples had been stored 11 months unopened at 2–8° C. prior to the above testing.
[b]High performance liquid chromatography assay was done using a TSK-3000SW column based on the published report by Bertolini, Vox Sang. 43:87 (1982). The flow rate was 0.5 ml/min and the detector wavelength was set at 280 nm. The aggregates, where present, were observed to elute at approximately 13.6 minutes, followed by a dimer peak at approximately 16.5 minutes and a monomer peak at approximately 19.5 minutes.

The data in Table V show that within the range of glycine concentrations of about 0.01M to about 0.5M the stabilizing effect of the present solutions is not dependent upon glycine concentration.

While the present invention has been described and exemplified primarily with reference to human gamma globulin, the stabilization techniques described hereinabove are applicable to other immunoglobulins as well. For example, whole native antibodies prepared using hybridoma technology such as that described in Niman et al., Proc. Nat'l Acad. Sci. U.S.A. 80:4949–4953 (1983), and in Hybridoma Techniques, EMBO, SKMB Course 1980, Basel, Cold Spring Harbor Laboratory, Cold Spring Harbor, Me., can also be advantageously stabilized as taught hereinabove, stored and utilized, inter alia, for diagnostic purposes. Moreover, monoclonal antibodies can be obtained not only from in vitro hybridoma culture supernatants, but also in generally more concentrated form from ascites fluid of mammals into which the desired hybridoma has been introduced. Again, the production of monoclonal antibodies using ascites fluid is well known in the art. However, such antibodies can be advantageously stabilized and stored for later use utilizing the features of this invention.

The foregoing discussion and the specific examples are intended as illustrative of the present invention and are not to be taken as limiting. Still other variations within the spirit and scope of this invention are possible and will readily present themselves to those skilled in the art.

We claim:

1. A stabilized immunoglobulin preparation comprising an aqueous solution of an immunoglobulin in a pharmacologically effective concentration; said solution being substantially free from anticomplement activity, containing histidine at a concentration sufficient to inhibit aggregation of said immunoglobulin, having a pH value of at least about 6.0 but not greater than 7.0 and a buffering capacity in that range; and a conductivity of about 2 to about 4 millisiemens at 5° C.

2. The preparation in accordance with claim 1 wherein the immunoglobulin concentration is no more than about 5 weight percent.

3. The preparation in accordance with claim 1 wherein the immunoglobulin concentration is about 0.05 to about 5 weight percent, histidine concentration is about 0.025M to about 0.2M, and the preparation additionally contains glycine in a concentration of about 0.05M to about 0.5M.

4. The preparation in accordance with claim 3 wherein the immunoglobulin concentration is about 1 to about 2 weight percent, histidine concentration is about 0.05M and glycine concentration is about 0.1M.

5. The preparation in accordance with claim 1 wherein the aqueous solution has a pH value of about 6.2 to about 6.6 and the conductivity is about 2.5 to about 3.5 millisiemens at 5° C.

6. The preparation in accordance with claim 1 wherein the aqueous solution has a pH value of about 6.4 and the conductivity is about 2.7 millisiemens at 5° C.

7. The preparation in accordance with claim 1 wherein the immunoglobulin is gamma globulin.

8. The preparation in accordance with claim 1 wherein the immunoglobulin is monoclonal antibody.

9. Stabilized gamma globulin composition which exhibits substantially no anticomplement activity and which comprises an aqueous solution containing about 0.05 to about 5 weight percent gamma globulin, histidine in a concentration sufficient to inhibit gamma globulin aggregation, and glycine in a concentration of about 0.05M to about 0.5M; said aqueous solution having a pH value of at least about 6.0 but no more than 7.0 and a conductivity of about 2 to about 4 millisiemens at 5° C., said histidine having a buffering capacity within the specified pH range.

10. The stabilized composition in accordance with claim 9 wherein the histidine is L-histidine.

11. The stabilized composition in accordance with claim 9 wherein the pH value of the solution is about 6.2 to about 6.6 and the conductivity is about 2.5 to about 3.5 millisiemens at 5° C.

12. The stabilized composition in accordance with claim 9 wherein the pH value of the solution is about 6.4 and the conductivity is about 2.7 millisiemens at 5° C.

13. The stabilized composition in accordance with claim 9 wherein the histidine is L-histidine and is present at a concentration of about 0.025M to about 0.2M.

14. The stabilized composition in accordance with claim 9 wherein the histidine is L-histidine and is present at a concentration of about 0.05M; wherein glycine is present at a concentration of about 0.1M; and wherein said aqueous solution has a pH value of about 6.4 and conductivity of about 2.7 millisiemens at 5° C.

15. The stabilized composition in accordance with claim 9 wherein gamma globulin is present in an amount of about 1 to about 2 weight percent; wherein the histidine is L-histidine and is present at a concentration of about 0.05M; wherein glycine is present at a concentration of about 0.1M; and wherein said aqueous solution has a pH value of about 6.4 and conductivity of about 2.7 millisiemens at 5° C.

16. A method for the stabilization of an immunoglobulin which comprises the steps of
providing an aqueous solution of an immunoglobulin;
combining with said solution histidine in an amount sufficient to inhibit aggregation of the immunoglobulin present, said histidine having a buffering capacity in the range of at least about 6 but not more than 7.0;
adjusting the hydrogen ion concentration of the resulting solution to a value of at least about 6.0 but not more than 7.0; and
adjusting, if necessary, the conductivity of the resulting solution to a value of about 2 to about 4 millisiemens at 5° C.

17. The method in accordance with claim 16 wherein the immunoglobulin is human gamma globulin having a purity of at least about 95 percent, wherein the histidine is L-histidine; and wherein the pH value of the resulting solution is adjusted to about 6.4 and the conductivity of the resulting solution is adjusted to about 2.7 millisiemens at 5° C.

18. The method in accordance with claim 17 wherein additionally glycine is combined with said solution in an amount sufficient to provide in the resulting solution a glycine concentration of about 0.05M to about 0.5M.

19. The method in accordance with claim 16 wherein the immunoglobulin is human gamma globulin having a purity of at least about 99.5 percent and present at a concentration of about 0.05 to about 5 weight percent, wherein L-histidine is combined with said solution in an amount providing a solution concentration of about 0.025M to about 0.2M, wherein additionally glycine is combined with said solution in an amount providing a solution concentration of about 0.05M to about 0.5M, wherein pH of the resulting solution is adjusted to a value of about 6.4, and wherein conductivity of the resulting solution is adjusted to 2.7 millisiemens at 5° C.

* * * * *